US005830477A

United States Patent [19]

Lathe et al.

[11] Patent Number: 5,830,477

[45] Date of Patent: Nov. 3, 1998

[54] VACCINE AGAINST RABIES AND PROCESS FOR PREPARATION THEREOF

[75] Inventors: Richard Lathe; Marie-Paule Kieny; Robert Drillien, all of Strasbourg; Jean-Pierre Lecocq, Reichsteet, all of France

[73] Assignee: Transgene S.A., Strasbourg, France

[21] Appl. No.: 480,736

[22] Filed: Jun. 7, 1995

Related U.S. Application Data

[63] Continuation of Ser. No. 231,457, Apr. 21, 1994, which is a continuation of Ser. No. 38,052, Mar. 29, 1993, abandoned, which is a continuation of Ser. No. 759,138, Sep. 11, 1991, abandoned, which is a continuation of Ser. No. 378,801, Jul. 11, 1989, abandoned, which is a continuation-in-part of Ser. No. 829,144, Dec. 24, 1985, abandoned.

[30] Foreign Application Priority Data

Apr. 25, 1984 [FR] France .................................... 84 06499

[51] Int. Cl.$^{6}$ .......................... A61K 39/205; C12N 7/01; C12N 15/47

[52] U.S. Cl. .................. 424/224.1; 424/93.2; 435/172.3; 435/235.1

[58] Field of Search ............................... 435/69.1, 172.3, 435/235.1; 424/93.2, 224.1, 818, 819, 821, 832

[56] References Cited

U.S. PATENT DOCUMENTS

| | | | |
|---|---|---|---|
| 4,393,201 | 7/1983 | Curtis et al. | 536/23.72 |
| 4,722,818 | 2/1988 | Paoletti et al. | 424/199.1 |

FOREIGN PATENT DOCUMENTS

| | | | |
|---|---|---|---|
| 2526661 | 5/1982 | European Pat. Off. | A61K 39/205 |
| 0083286 | 6/1983 | European Pat. Off. | C12N 15/00 |
| 2552776 | 10/1983 | European Pat. Off. | C12N 15/00 |
| 2562090 | 3/1984 | European Pat. Off. | C12P 21/00 |

OTHER PUBLICATIONS

M.P. Kieny et al., *Nature* 312:163–166 (Nov. 8, 1984)m "Expression of rabies virus glycoprotein from a recomb. vaccinia virus".

T.J. Wiktor et al., *P.N.A.S.* 81:7194–7198 (Nov. 1984), "Protection from rabies by a vaccinia virus recombinant containing the rabies virus glycoprotein gene".

*Nature* 336:416 (Dec. 1, 1987), "New vaccine and initiative mean end of rabies in sight for Europe?".

*Wistar News Release*, May 3, 1988, "The Wistar Institute announces new recombinant rabies vaccine trials in Western Europe, plans for U.S. trial".

*International Herald Tribune*, Thursday, May 19, 1988, "Rabies Vaccine Ready for Testing".

*News/Sun–Sentinel*, Thursday, May 5, 1988, "U.S. Test Sought of Vaccine".

*DHHS Research Resources Report*, vol. X, No. 4, Apr. 1986, "Recombinant DNA Research and Wildlife Studies Focus on Reducing the Spread of Rabies".

Paoletti et al., *P.N.A.S.* 81:193–197 (1984).

Panicali et al., *P.N.A.S.* 80:5364–5368 (1983).

Smith et al., *P.N.A.S.* 80:7155–7159 (1983).

Dietzschold et al., *J. Virol.* 44:595–602 (1982).

Verma, *Biochim. Biophys. Acta* 473:1–38 (1977).

Keller et al. (1980), Annales de Virologie 31(1):85–94 (Abstract only).

*Primary Examiner*—Nancy Degen

*Attorney, Agent, or Firm*—Burns, Doane, Swecker & Mathis, L.L.P.

[57] ABSTRACT

The present invention relates to a vaccinia virus, characterized in that it contains all or part of a DNA sequence (I) coding for an antigenic glycoprotein of rabies.

36 Claims, 14 Drawing Sheets

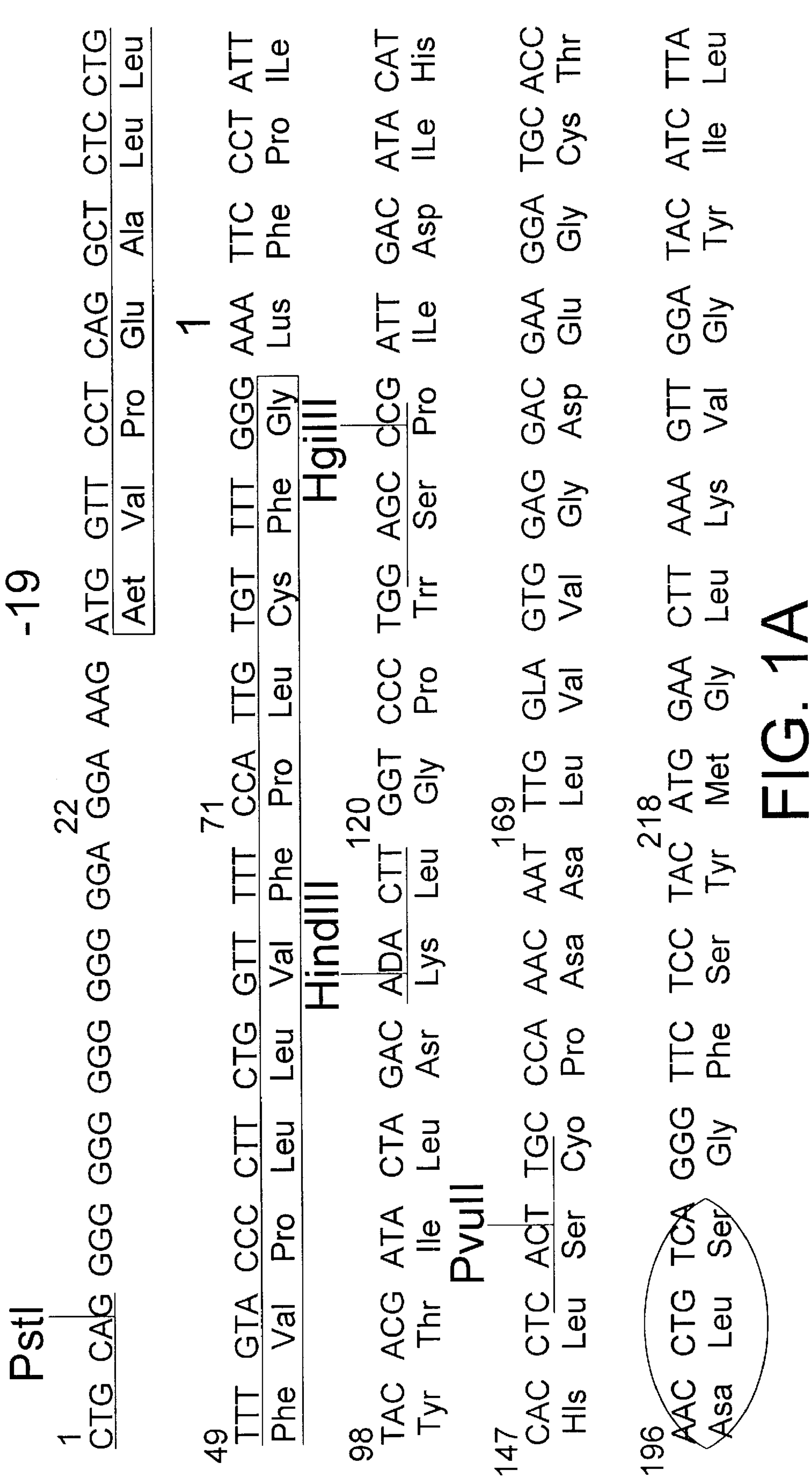

FIG. 1A

```
        Pstl
      1
      CTG CAG GGG GGG GGG GGA GGA AAG ATG GTT CCT CAG GCT CTC CTG
                                        Aet Val Pro Glu Ala Leu Leu
                    22                  -19  1

      49
      TTT GTA CCC CTT CTG GTT TTT CCA TTG TGT TTT GGG AAA TTC CCT ATT
      Phe Val Pro Leu Leu Val Phe Pro Leu Cys Phe Gly Lus Phe Pro ILe
                          71            HindIII       HgiIII

      98
      TAC ACG ATA CTA GAC CTT GGT CCC TGG AGC CCG ATT GAC ATA CAT
      Tyr Thr Ile Leu Asr Leu Gly Pro Trr Ser Pro ILe Asp ILe His
                      120                 ADA
                      HindIII

      147
      CAC CTC ACT TGC CCA AAC AAT TTG GLA GTG GAG GAC GAA GGA TGC ACC
      His Leu Ser Cyo Pro Asa Asa Leu Val Gly Asp Glu Gly Cys Thr
              PvuII                169

      196
      AAC CTG TCA GGG TTC TCC TAC ATG GAA CTT AAA GTT GGA TAC ATC TTA
      Asa Leu Ser Gly Phe Ser Tyr Met Gly Leu Lys Val Gly Tyr ILe Leu
                      218
```

245 ... 266

GCC ATA AAA ATG AAC GGG TTC ACT TGC ACA GGC GTT GTG ACG GAG GCT

Ala ILe Lys Het Asp Gly Phe Thr Lys Thr Gly Val Val Thr Gly Ala

293 ... 314

GAA ACC TAC ACT AAC TTC GTT GGT TAT GTC ACA ACC ACG TTC AAA AGA

Glu Thr Tyr Thr Asp Phe Val Gly Tyr Val Thr Thr Thr Phe Lys Arg

AvaIII

341 ... 362

AAG CAT TTC CGC CCA ACA CCA GAL GCG TGT AGA GCC GCG TAC AAC TGG

Lys HIs Phe Arg Pro Thr Pro Asp Ala Cys Arg Ala Ala Tyr Asa Trr

*HpaII*BstEII

389 ... 410

AAG ATG GCC AAC GAC CCC AGA TAT GAA GAG TCT CTA CAC AAT CCG TAC

Lys Hel Ala Gly Asp Pro Arg Tyr Glu Glu Ser Leu His Asa Pro Tyr

AsuII

437 ... 458

CCT GAC TAC CGC TGG CTT CGG ACT GTA AAA ACC ACC AAG GAG TCT CTC

Pro Asp Tyr Arg Tre Leu Arg Thr Val Lys Thr Thr Lys Gly Ser Leu

FIG. 1B

```
485                                          506
 GTT ATC ATA TCT CCA AGT GTA GCA GAT TTG GAC CCA TAT GAC AGA TCC
 Val Ile Ile Ser Pro Ser Val Ala Asp Leu Asp Pro Tyr Asp Arg Ser
     XhoI AvaI
533                                          554
 CTT CAC TCG AGG BTC TTC CCT AGC GGG AAG TGC TCA GGA GTA GCG GTG
 Leu His Ser Arg Val Phe Pro Ser Gly Lys Cys Ser Gly Val Ala Val
                                                              AvaI
581                                          602
 TCT TCT ACC TAC TGC TCC ACT AAC CAC GAT TAC ACC ATT TGG ATG CCC
 Ser Ser Thr Tyr Cyg Ser Thr Asa His Asp Tyr Thr ILe Trr Het Pro

629                                          650
 GAG AAT CCG AGA CTA GGG ATG TCT TGT GAC ATT TTT ACC AAT AGT AGT
 Glu Asa Pro Arg Leu Gly Hat Ser Cys Asp ILe Phe Thr Asa Ser Arg

677                                          698
 GGG AAG AGA GCA TCC AAA GGG AGT GAG ACT TGC GGC TTT GTA GAT GAA
 Gly Lys Arg Ala Ser Lys Gly Ser Gly Thr Cys Gly Phe Val Asp Gly
```

FIG. 1C

StuI *HaeI* AhaIII SphI 725 746
AGA GGC CTA TAT AAG TCT TTA AAA GGA GCA TGC AAA CTC AAG TTA TGT
Arg Gly Leu Tyr Lys Ser Leu Lys Lys Ala Cys Lys Leu Lys Leu Cys

NruI 773 794
GGA GTT CTA GGA CTT AGA CTT ATG GAT GGA ACA TGG GTC GCG ATG CAA
Gly Val Leu Gly Leu Arg Leu Met Asp Gly Thr Gre Val Als Met Gln 821 842
ACA TCA AAT GAA ACC AAA TGG TGC CCT CCC GAT CAG TTG GTG AAC CTG
Thr Ser Asa Gly The Lys Trr Cws Pro Pro Asp Gln Leu Val Asp Leu 869 890
CAC GAC TTT CGC TCA GAC GAA ATT GAG CAC CTT GTT GTA GAG GAG TTG
His Asp Phe Arg Ser Asp Gly ILe Glu His Leu Val Val Gly Glu Leu

BgaI 917 938
GTC AGG AAG AGA GAG GAG TGT CTG GAT GCA CTA GAG TCC ATC ATG ACA
Val Arg Lws Arg Glu Glu Cys Leu Asp Ala Leu Gly Ser ILe Met Thr

FIG. 1D

Acyl

```
965                                      986
   ACC AAG TCA GTG AGT TTL AGA CGT CTC AGT CAT TTA AGA AAA CCT GTC
   Thr Lys Ser Val Ser Phe Arg Arg Leu Ser His Leu Arg Lys Leu Val

1013                                     1034
   CCT GGG TTT GGG AAA GCA TAT ACC ATA TTC AAC AAG ACC TTG ATG GAA
   Pro Gly Phe Glu Lys Ala Tyr Thr ILe Phe Asa Lys Thr Leu Met Gly

1061                                     1082
   GCC GAT GCT CAC TAC AAG TCA GTC AGA ACT TGG AAT GAG ATC CTC CCT
   Ala Asp Ala His Tyr Lys Ser Val Arg Thr Trr Asp Glu Ile Leu Pro

1109                                     1130
   TCA AAA GGG TGT TTA AGA GTT GGG GGG AGG TGT CAT CCT CAT GTG AAC
   Ser Lys Gly Cys Leu Arg Val Gly Gly Arg Cys His Pro His Val Asn

1157                                     1178
   GGG GTG TTT TTC AAT GGT ATA ATA TTA GGA CCT GAC GGC AAT GTC TTA
   Gly Val Phe Phe Asp Gly ILe ILe Leu Gly Pro Asp Gly Asn Val Leu
```

FIG. 1E

```
1205                                      1226
  ACT CCA GAG ATG CAA TCA TCC CTC CTC CAG CAA CAT ATG GAG TTG TTG
  ILe Pro Gly Het Glu Ser Ser Leu Leu Gln Gln His Het Glu Leu Leu
                                                          AccI
1253                                      1274
  GAA TCC TCG GTT ATC CCC CTT GTG CAC CCC CTG GCA GAC CCG TCT ACC
  Glu Ser Ser Val ILe Pro Leu Val His Pro Leu Ala Asp Pro Ser Thr

1301                                      1322
  GTT TTC AAG GAC GGT GAC GAG GCT GAG GAT TTT GTT GAA GTT CAC CTT
  Val Phe Lys Asp Gly Asp Glu Ala Glu Asp Phe Val Glu Val His Leu
                                            HindII
1349                                      1370
  CCC GAT GTG CAC AAT CAG GTC TCA GGA GTT GAC TTG GGT CTC CCG AAC
  Pro Asp Val His Asn Gln Val Ser Glu Gll Asp Leu Gly Leu Pro Asp
                                             ApaI Hgl III
1397                                      1418
  TGG GGG AAG TAT GTA TTA CTG AGT GCA GGG GCC CTG ACT GCC TTG ATG
  Trr Gly Lys Tyr Val Leu Leu Ser Ala Gly Ala Leu Thr Ala Leu Het
```

FIG. 1F

```
1445                                        1466
TTG  ATA  ATT  TTC  CTG  ATG  ACA  TGT  TGT  AGA  AGA  GTC  AAT  CGA  TCA  GAA
Leu  ILe  ILe  Phe  Leu  Het  Thr  Cys  Cys  Arg  Arg  Val  Asp  Arg  Ser  Glu

1493                                        1514
CCT  ACG  CAA  CAC  AAT  CTC  AGA  GGG  ACA  GGG  AGG  GAG  GTG  TCA  GTC  ACT
Pro  Thr  Gln  His  Asa  Leu  Arg  Gly  Thr  Gly  Arg  Gly  Val  Ser  Val  Thr

1541                                        1562
CCC  CAA  AGC  GGG  AAG  ATC  ATA  TCT  TCA  TGG  GAA  TCA  CAC  AAG  AGT  GGG
Pro  Glu  Ser  Gly  Lys  ILe  ILe  Ser  Ser  Trr  Gly  Ser  His  Lys  Ser  Gly
                    505
1589                                        1610
GGT  GAG  ACC  ABA  CTG  TGA  GGA  CTG  GCC  GTC  CTT  TCA  ACG  ATC  CAA  GTC
Gly  Gly  Thr  Arg  Leu  ***

1637                                        1658
CTG  AAG  ATC  ACC  TCC  CCT  TGG  GGG  GTT  CTT  TTT  AAA  AAA  AAA  AAA  AAA
                                             PstI
1685                                        1706
AAA  AAA  AAA  ACC  CCC  CCC  CCC  CCC  CTG  CAG
```

FIG. 1G

```
                                            Met Val Pro Gln Ala
CTGCAG ———— G₂₃ ———— AGGAAAGATGGTT CCT CAG GCT ———— A
  PstI                                       ↑MstII

                        5'GATCTAATATGGTTCC3'
                        3'ATTATACCAAGGAGT5'              B

                        AGATCTAATATGGTT CCT CAG GCT ———— C
                          BglII              MstII
                        plg 155
```

```
EcoRI     BglII                                                HindIII
                    Met ------------- TyrThrILeLEUAspLysLeu ----
GAATTC --- AGATCT--- ATG ------------- TACACGATACTAGACAAGCTT ----

                                       *    *
                         5' - TACACGATCCCAGACAAGC - 3'
                                  * * * *

EcoRI     BglII                                                HindIII
                    Met ------------- TyrThrILePROAspLysLeu ----
GAATTC --- AGATCT--- ATG ------------- TACACGATCCCAGACAAGCTT ----
```

FIG. 3

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 1710 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
( A ) ORGANISM: Rhabdovirus
( B ) STRAIN: ERA ( i x ) FEATURE:
( A ) NAME/KEY: CDS
( B ) LOCATION: 28..1602

-continued (ix) FEATURE:
(A) NAME/KEY: mat_peptide
(B) LOCATION: 85..1602

(ix) FEATURE:
(A) NAME/KEY: misc_feature
(B) LOCATION: 28..1602
(D) OTHER INFORMATION: /note= "cDNA for rabies glycoprotein (Leu-8) precursor."

(x) PUBLICATION INFORMATION:
(A) AUTHORS: ANILIONIS, A. et al
(C) JOURNAL: Nature
(D) VOLUME: 291
(F) PAGES: 275-278
(G) DATE: 1981

(xi) SEQUENCE DESCRIPTION: SEQ ID NO:1:

```
CTGCAGGGGG GGGGGGGGGG AGGAAAG ATG GTT CCT CAG GCT CTC CTG TTT    51
                              Met Val Pro Gln Ala Leu Leu Phe
                              -19             -15

GTA CCC CTT CTG GTT TTT CCA TTG TGT TTT GGG AAA TTC CCT ATT TAC    99
Val Pro Leu Leu Val Phe Pro Leu Cys Phe Gly Lys Phe Pro Ile Tyr
    -10                  -5                      1               5

ACG ATA CTA GAC AAG CTT GGT CCC TGG AGC CCG ATT GAC ATA CAT CAC   147
Thr Ile Leu Asp Lys Leu Gly Pro Trp Ser Pro Ile Asp Ile His His
                10                  15                  20

CTC AGT TGC CCA AAC AAT TTG GTA GTG GAG GAC GAA GGA TGC ACC AAC   195
Leu Ser Cys Pro Asn Asn Leu Val Val Glu Asp Glu Gly Cys Thr Asn
            25                  30                  35

CTG TCA GGG TTC TCC TAC ATG GAA CTT AAA GTT GGA TAC ATC TTA GCC   243
Leu Ser Gly Phe Ser Tyr Met Glu Leu Lys Val Gly Tyr Ile Leu Ala
        40                  45                  50

ATA AAA ATG AAC GGG TTC ACT TGC ACA GGC GTT GTG ACG GAG GCT GAA   291
Ile Lys Met Asn Gly Phe Thr Cys Thr Gly Val Val Thr Glu Ala Glu
    55                  60                  65

ACC TAC ACT AAC TTC GTT GGT TAT GTC ACA ACC ACG TTC AAA AGA AAG   339
Thr Tyr Thr Asn Phe Val Gly Tyr Val Thr Thr Thr Phe Lys Arg Lys
70                  75                  80                  85

CAT TTC CGC CCA ACA CCA GAT GCG TGT AGA GCC GCG TAC AAC TGG AAG   387
His Phe Arg Pro Thr Pro Asp Ala Cys Arg Ala Ala Tyr Asn Trp Lys
                90                  95                 100

ATG GTC GGT GAC CCC AGA TAT GAA GAG TCT CTA CAC AAT CCG TAC CCT   435
Met Val Gly Asp Pro Arg Tyr Glu Glu Ser Leu His Asn Pro Tyr Pro
            105                 110                 115

GAC TAC CGC TGG CTT CGG ACT GTA AAA ACC ACC AAG GAG TCT CTC GTT   483
Asp Tyr Arg Trp Leu Arg Thr Val Lys Thr Thr Lys Glu Ser Leu Val
        120                 125                 130

ATC ATA TCT CCA AGT GTA GCA GAT TTG GAC CCA TAT GAC AGA TCC CTT   531
Ile Ile Ser Pro Ser Val Ala Asp Leu Asp Pro Tyr Asp Arg Ser Leu
    135                 140                 145

CAC TCG AGG GTC TTC CCT AGC GGG AAG TGC TCA GGA GTA GCG GTG TCT   579
His Ser Arg Val Phe Pro Ser Gly Lys Cys Ser Gly Val Ala Val Ser
150                 155                 160                 165

TCT ACC TAC TGC TCC ACT AAC CAC GAT TAC ACC ATT TGG ATG CCC GAG   627
Ser Thr Tyr Cys Ser Thr Asn His Asp Tyr Thr Ile Trp Met Pro Glu
                170                 175                 180

AAT CCG AGA CTA GGG ATG TCT TGT GAC ATT TTT ACC AAT AGT AGA GGG   675
Asn Pro Arg Leu Gly Met Ser Cys Asp Ile Phe Thr Asn Ser Arg Gly
            185                 190                 195

AAG AGA GCA TCC AAA GGG AGT GAG ACT TGC GGC TTT GTA GAT GAA AGA   723
Lys Arg Ala Ser Lys Gly Ser Glu Thr Cys Gly Phe Val Asp Glu Arg
        200                 205                 210

GGC CTA TAT AAG TCT TTA AAA GGA GCA TGC AAA CTC AAG TTA TGT GGA   771
```

-continued

Gly Leu Tyr Lys Ser Leu Lys Gly Ala Cys Lys Leu Lys Leu Cys Gly
215 220 225

GTT CTA GGA CTT AGA CTT ATG GAT GGA ACA TGG GTC GCG ATG CAA ACA 819
Val Leu Gly Leu Arg Leu Met Asp Gly Thr Trp Val Ala Met Gln Thr
230 235 240 245

TCA AAT GAA ACC AAA TGG TGC CCT CCC GAT CAG TTG GTG AAC CTG CAC 867
Ser Asn Glu Thr Lys Trp Cys Pro Pro Asp Gln Leu Val Asn Leu His
250 255 260

GAC TTT CGC TCA GAC GAA ATT GAG CAC CTT GTT GTA GAG GAG TTG GTC 915
Asp Phe Arg Ser Asp Glu Ile Glu His Leu Val Val Glu Glu Leu Val
265 270 275

AGG AAG AGA GAG GAG TGT CTG GAT GCA CTA GAG TCC ATC ATG ACA ACC 963
Arg Lys Arg Glu Glu Cys Leu Asp Ala Leu Glu Ser Ile Met Thr Thr
280 285 290

AAG TCA GTG AGT TTC AGA CGT CTC AGT CAT TTA AGA AAA CTT GTC CCT 1011
Lys Ser Val Ser Phe Arg Arg Leu Ser His Leu Arg Lys Leu Val Pro
295 300 305

GGG TTT GGA AAA GCA TAT ACC ATA TTC AAC AAG ACC TTG ATG GAA GCC 1059
Gly Phe Gly Lys Ala Tyr Thr Ile Phe Asn Lys Thr Leu Met Glu Ala
310 315 320 325

GAT GCT CAC TAC AAG TCA GTC AGA ACT TGG AAT GAG ATC CTC CCT TCA 1107
Asp Ala His Tyr Lys Ser Val Arg Thr Trp Asn Glu Ile Leu Pro Ser
330 335 340

AAA GGG TGT TTA AGA GTT GGG GGG AGG TGT CAT CCT CAT GTG AAC GGG 1155
Lys Gly Cys Leu Arg Val Gly Gly Arg Cys His Pro His Val Asn Gly
345 350 355

GTG TTT TTC AAT GGT ATA ATA TTA GGA CCT GAC GGC AAT GTC TTA ATC 1203
Val Phe Phe Asn Gly Ile Ile Leu Gly Pro Asp Gly Asn Val Leu Ile
360 365 370

CCA GAG ATG CAA TCA TCC CTC CTC CAG CAA CAT ATG GAG TTG TTG GAA 1251
Pro Glu Met Gln Ser Ser Leu Leu Gln Gln His Met Glu Leu Leu Glu
375 380 385

TCC TCG GTT ATC CCC CTT GTG CAC CCC CTG GCA GAC CCG TCT ACC GTT 1299
Ser Ser Val Ile Pro Leu Val His Pro Leu Ala Asp Pro Ser Thr Val
390 395 400 405

TTC AAG GAC GGT GAC GAG GCT GAG GAT TTT GTT GAA GTT CAC CTT CCC 1347
Phe Lys Asp Gly Asp Glu Ala Glu Asp Phe Val Glu Val His Leu Pro
410 415 420

GAT GTG CAC AAT CAG GTC TCA GGA GTT GAC TTG GGT CTC CCG AAC TGG 1395
Asp Val His Asn Gln Val Ser Gly Val Asp Leu Gly Leu Pro Asn Trp
425 430 435

GGG AAG TAT GTA TTA CTG AGT GCA GGG GCC CTG ACT GCC TTG ATG TTG 1443
Gly Lys Tyr Val Leu Leu Ser Ala Gly Ala Leu Thr Ala Leu Met Leu
440 445 450

ATA ATT TTC CTG ATG ACA TGT TGT AGA AGA GTC AAT CGA TCA GAA CCT 1491
Ile Ile Phe Leu Met Thr Cys Cys Arg Arg Val Asn Arg Ser Glu Pro
455 460 465

ACG CAA CAC AAT CTC AGA GGG ACA GGG AGG GAG GTG TCA GTC ACT CCC 1539
Thr Gln His Asn Leu Arg Gly Thr Gly Arg Glu Val Ser Val Thr Pro
470 475 480 485

CAA AGC GGG AAG ATC ATA TCT TCA TGG GAA TCA CAC AAG AGT GGG GGT 1587
Gln Ser Gly Lys Ile Ile Ser Ser Trp Glu Ser His Lys Ser Gly Gly
490 495 500

GAG ACC AGA CTG TGA GGACTGGCCG TCCTTTCAAC GATCCAAGTC CTGAAGATCA 1642
Glu Thr Arg Leu *
505

CCTCCCCTTG GGGGGTTCTT TTTAAAAAAA AAAAAAAAAA AAAAAAAACC CCCCCCCCCC 1702

CCCTGCAG 1710

-continued ( 2 ) INFORMATION FOR SEQ ID NO:2:

( i ) SEQUENCE CHARACTERISTICS:
( A ) LENGTH: 29 base pairs
( B ) TYPE: nucleic acid
( C ) STRANDEDNESS: double
( D ) TOPOLOGY: circular ( i i ) MOLECULE TYPE: other nucleic acid
( A ) DESCRIPTION: /desc = "portion of plasmid pTG150"

( i x ) FEATURE:
( A ) NAME/KEY: CDS
( B ) LOCATION: 15..29

( i x ) FEATURE:
( A ) NAME/KEY: misc_feature
( B ) LOCATION: 15..29
( D ) OTHER INFORMATION: /note= "5'end of rabies glycoprotein cDNA inserted into plasmid pTG150."

( i x ) FEATURE:
( A ) NAME/KEY: mat_peptide
( B ) LOCATION: 27..29

( x i ) SEQUENCE DESCRIPTION: SEQ ID NO:2:

```
CTGCAGGAGG AAAG ATG GTT CCT CAG GCT                 29
                Met Val Pro Gln Ala
                 -4              1
```

( 2 ) INFORMATION FOR SEQ ID NO:3:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "oligonucleotide"

( x i ) SEQUENCE DESCRIPTION: SEQ ID NO:3:

GATCTAATAT GGTTCC 16

( 2 ) INFORMATION FOR SEQ ID NO:4:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "oligonucleotide"

( x i ) SEQUENCE DESCRIPTION: SEQ ID NO:4:

ATTATACCAA GGAGT 15

( 2 ) INFORMATION FOR SEQ ID NO:5:

( i ) SEQUENCE CHARACTERISTICS:
( A ) LENGTH: 24 base pairs
( B ) TYPE: nucleic acid
( C ) STRANDEDNESS: double
( D ) TOPOLOGY: circular ( i i ) MOLECULE TYPE: other nucleic acid
( A ) DESCRIPTION: /desc = "portion of plasmid pTG155"

( i x ) FEATURE:
( A ) NAME/KEY: misc_feature
( B ) LOCATION: 1..24
( D ) OTHER INFORMATION: /note= "Insert of SEQ ID NOS.: 3 and 4 between BgdII and MstII for pTG155."

( x i ) SEQUENCE DESCRIPTION: SEQ ID NO:5:

AGATCTAATA TGGTTCCTCA GGCT 24

( 2 ) INFORMATION FOR SEQ ID NO:6:

( i ) SEQUENCE CHARACTERISTICS:
( A ) LENGTH: 6 base pairs
( B ) TYPE: nucleic acid
( C ) STRANDEDNESS: double
( D ) TOPOLOGY: linear ( i i ) MOLECULE TYPE: other nucleic acid ( i x ) FEATURE:
( A ) NAME/KEY: misc_feature
( B ) LOCATION: 1..6
( D ) OTHER INFORMATION: /note= "EcoRI site."

( x i ) SEQUENCE DESCRIPTION: SEQ ID NO:6:

GAATTC 6

( 2 ) INFORMATION FOR SEQ ID NO:7:

( i ) SEQUENCE CHARACTERISTICS:
( A ) LENGTH: 6 base pairs
( B ) TYPE: nucleic acid
( C ) STRANDEDNESS: double
( D ) TOPOLOGY: linear ( i i ) MOLECULE TYPE: other nucleic acid ( i x ) FEATURE:
( A ) NAME/KEY: misc_feature
( B ) LOCATION: 1..6
( D ) OTHER INFORMATION: /note= "BghII site."

( x i ) SEQUENCE DESCRIPTION: SEQ ID NO:7:

AGATCT 6

( 2 ) INFORMATION FOR SEQ ID NO:8:

( i ) SEQUENCE CHARACTERISTICS:
( A ) LENGTH: 21 base pairs
( B ) TYPE: nucleic acid
( C ) STRANDEDNESS: double
( D ) TOPOLOGY: circular ( i i ) MOLECULE TYPE: cDNA to mRNA ( i x ) FEATURE:
( A ) NAME/KEY: CDS
( B ) LOCATION: 1..21

( i x ) FEATURE:
( A ) NAME/KEY: mutation
( B ) LOCATION: replace(5..11, "")
( D ) OTHER INFORMATION: /note= "Portion of pTG155 encoding residues 5 through 11 of rabies glycoprotein G (with leucine at position 8)."

( i x ) FEATURE:
( A ) NAME/KEY: misc_feature
( B ) LOCATION: 1..21
( D ) OTHER INFORMATION: /note= "Portion of pTG155 encoding residues 5 through 11 of rabies glycoprotein G (with leucine at position 8)."

( x i ) SEQUENCE DESCRIPTION: SEQ ID NO:8:

TAC ACG ATA CTA GAC AAG CTT 21
Tyr Thr Ile Leu Asp Lys Leu
5

-continued ( 2 ) INFORMATION FOR SEQ ID NO:9:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "oligonucleotide"

( i x ) FEATURE:
( A ) NAME/KEY: misc_feature
( B ) LOCATION: 1..19
( D ) OTHER INFORMATION: /note= "DNA used to convert leucine to proline at position 8 of rabies glycoprotein."

( x i ) SEQUENCE DESCRIPTION: SEQ ID NO:9:

TACACGATCC CAGACAAGC 19

( 2 ) INFORMATION FOR SEQ ID NO:10:

( i ) SEQUENCE CHARACTERISTICS:
( A ) LENGTH: 21 base pairs
( B ) TYPE: nucleic acid
( C ) STRANDEDNESS: double
( D ) TOPOLOGY: circular ( i i ) MOLECULE TYPE: cDNA to mRNA ( i x ) FEATURE:
( A ) NAME/KEY: CDS
( B ) LOCATION: 1..21

( i x ) FEATURE:
( A ) NAME/KEY: mutation
( B ) LOCATION: replace(5..11, "")
( D ) OTHER INFORMATION: /note= "Mutated site in PTG155-Pro and encoded amino acids. Portion of TG155 encoding residues 5- 11 of rabies glycoprotein G (with proline at position 8)."

( x i ) SEQUENCE DESCRIPTION: SEQ ID NO:10:

```
TAC ACG ATC CCA GAC AAG CTT                21
Tyr Thr Ile Pro Asp Lys Leu
         10
```

( 2 ) INFORMATION FOR SEQ ID NO:11:

( i ) SEQUENCE CHARACTERISTICS:
( A ) LENGTH: 8 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "oligonucleotide"

( i x ) FEATURE:
( A ) NAME/KEY: misc_feature
( B ) LOCATION: 1..8
( D ) OTHER INFORMATION: /note= "BghII linker."

( x i ) SEQUENCE DESCRIPTION: SEQ ID NO:11:

CAGATCTG 8

( 2 ) INFORMATION FOR SEQ ID NO:12:

( i ) SEQUENCE CHARACTERISTICS:
( A ) LENGTH: 524 amino acids
( B ) TYPE: amino acid
( D ) TOPOLOGY: linear -continued ( i i ) MOLECULE TYPE: protein ( x i ) SEQUENCE DESCRIPTION: SEQ ID NO:12:

Met Val Pro Gln Ala Leu Leu Phe Val Pro Leu Leu Val Phe Pro Leu
-19 -15 -10 -5

Cys Phe Gly Lys Phe Pro Ile Tyr Thr Ile Leu Asp Lys Leu Gly Pro
1 5 10

Trp Ser Pro Ile Asp Ile His His Leu Ser Cys Pro Asn Asn Leu Val
15 20 25

Val Glu Asp Glu Gly Cys Thr Asn Leu Ser Gly Phe Ser Tyr Met Glu
30 35 40 45

Leu Lys Val Gly Tyr Ile Leu Ala Ile Lys Met Asn Gly Phe Thr Cys
50 55 60

Thr Gly Val Val Thr Glu Ala Glu Thr Tyr Thr Asn Phe Val Gly Tyr
65 70 75

Val Thr Thr Thr Phe Lys Arg Lys His Phe Arg Pro Thr Pro Asp Ala
80 85 90

Cys Arg Ala Ala Tyr Asn Trp Lys Met Val Gly Asp Pro Arg Tyr Glu
95 100 105

Glu Ser Leu His Asn Pro Tyr Pro Asp Tyr Arg Trp Leu Arg Thr Val
110 115 120 125

Lys Thr Thr Lys Glu Ser Leu Val Ile Ile Ser Pro Ser Val Ala Asp
130 135 140

Leu Asp Pro Tyr Asp Arg Ser Leu His Ser Arg Val Phe Pro Ser Gly
145 150 155

Lys Cys Ser Gly Val Ala Val Ser Ser Thr Tyr Cys Ser Thr Asn His
160 165 170

Asp Tyr Thr Ile Trp Met Pro Glu Asn Pro Arg Leu Gly Met Ser Cys
175 180 185

Asp Ile Phe Thr Asn Ser Arg Gly Lys Arg Ala Ser Lys Gly Ser Glu
190 195 200 205

Thr Cys Gly Phe Val Asp Glu Arg Gly Leu Tyr Lys Ser Leu Lys Gly
210 215 220

Ala Cys Lys Leu Lys Leu Cys Gly Val Leu Gly Leu Arg Leu Met Asp
225 230 235

Gly Thr Trp Val Ala Met Gln Thr Ser Asn Glu Thr Lys Trp Cys Pro
240 245 250

Pro Asp Gln Leu Val Asn Leu His Asp Phe Arg Ser Asp Glu Ile Glu
255 260 265

His Leu Val Val Glu Glu Leu Val Arg Lys Arg Glu Glu Cys Leu Asp
270 275 280 285

Ala Leu Glu Ser Ile Met Thr Thr Lys Ser Val Ser Phe Arg Arg Leu
290 295 300

Ser His Leu Arg Lys Leu Val Pro Gly Phe Gly Lys Ala Tyr Thr Ile
305 310 315

Phe Asn Lys Thr Leu Met Glu Ala Asp Ala His Tyr Lys Ser Val Arg
320 325 330

Thr Trp Asn Glu Ile Leu Pro Ser Lys Gly Cys Leu Arg Val Gly Gly
335 340 345

Arg Cys His Pro His Val Asn Gly Val Phe Phe Asn Gly Ile Ile Leu
350 355 360 365

Gly Pro Asp Gly Asn Val Leu Ile Pro Glu Met Gln Ser Ser Leu Leu
370 375 380

Gln Gln His Met Glu Leu Leu Glu Ser Ser Val Ile Pro Leu Val His

-continued

| | | | | | | | | | | | | | | | |
|---|---|---|---|---|---|---|---|---|---|---|---|---|---|---|---|
| | | | 385 | | | | | 390 | | | | | 395 | | |
| Pro | Leu | Ala | Asp | Pro | Ser | Thr | Val | Phe | Lys | Asp | Gly | Asp | Glu | Ala | Glu |
| | | 400 | | | | | 405 | | | | | 410 | | | |
| Asp | Phe | Val | Glu | Val | His | Leu | Pro | Asp | Val | His | Asn | Gln | Val | Ser | Gly |
| | 415 | | | | | 420 | | | | | 425 | | | | |
| Val | Asp | Leu | Gly | Leu | Pro | Asn | Trp | Gly | Lys | Tyr | Val | Leu | Leu | Ser | Ala |
| 430 | | | | | 435 | | | | | 440 | | | | | 445 |
| Gly | Ala | Leu | Thr | Ala | Leu | Met | Leu | Ile | Ile | Phe | Leu | Met | Thr | Cys | Cys |
| | | | | 450 | | | | | 455 | | | | | 460 | |
| Arg | Arg | Val | Asn | Arg | Ser | Glu | Pro | Thr | Gln | His | Asn | Leu | Arg | Gly | Thr |
| | | | 465 | | | | | 470 | | | | | 475 | | |
| Gly | Arg | Glu | Val | Ser | Val | Thr | Pro | Gln | Ser | Gly | Lys | Ile | Ile | Ser | Ser |
| | | 480 | | | | | 485 | | | | | 490 | | | |
| Trp | Glu | Ser | His | Lys | Ser | Gly | Gly | Glu | Thr | Arg | Leu | | | | |
| | 495 | | | | | 500 | | | | | 505 | | | | |

VACCINE AGAINST RABIES AND PROCESS FOR PREPARATION THEREOF

This application is a continuation of application Ser. No. 8/231,457, filed Apr. 21, 1994 which is a continuation of application Ser. No. 08/038,052, filed Mar. 29, 1993, now abandoned: which is a continuation of application Ser. No. 07/759,138, filed Sep. 11, 1991, now abandoned; which is a continuation of application Ser. No. 07/378,801, filed Jul. 11, 1998, now abandoned; and which is a continuation in part of application Ser. No. 06/829,144, filed Dec. 24, 1985, now abandoned.

BACKGROUND

Rabies is a very ancient disease, but it has not hitherto been possible to effect complete control thereof. Although there are effective vaccines against rabies, such vaccines are too costly to be usable preventively. Moreover a very important reservoir of rabies virus exists in wild animals, and for this reason only island countries such as Great Britain and Japan have managed to eradicate this scurge.

The causative agent of this disease is a rhabdovirus. The transmission of rabies generally involves a receptor individual being bitten by an infected animal; the change in behaviour associated with chronic infection has an important role in the etiology of the disease.

In man, infection is followed by a dormancy period during which the virus travels through the nervous system to the brain. At the beginning, this disease can be treated effectively by intensive vaccination; however, when the behaviour symptoms appear, death is almost inevitable.

The virus contains 5 viral proteins, only one of which, the glycoprotein (G, haemagglutinin), passes through the lipid bilayer sheathing the virus. Thus, the glycoprotein is the only viral component capable of reacting with antibodies which neutralise the virus, and also of inducing production thereof. Anilionis et al. (1981) have described the isolation of a coding sequence corresponding to the messenger RNA of the glycoprotein of rabies strain ERA, and Lathe et al. (1984) have described the expression of this sequence in a bacterium.

Similar results have been reported by Yelverton et al. (1983) using a second rabies strain, CVS.

However, it has not yet been possible to carry out effective immunisation against rabies virus using the material synthesised by the bacteria.

Preliminary results suggest that post-translational modifications and/or presentation of the glycoprotein are important parameters in the use of this antigen to confer protection against rabies virus.

The present invention describes the expression of a sequence coding for the rabies glycoprotein in an environment such that correct modification and presentation of the primary translation products can take place.

Two groups have recently demonstrated the use of living recombinants of vaccinia virus to express the influenza or hepatitis B antigen for immunisation against these diseases (Smith et al., 1983; Panicali et al., 1983).

The expression of a sequence coding for an exogenous protein in vaccinia virus (VV) necessarily involves two stages:

1) The coding sequence must be aligned with a VV promoter and be inserted in a non-essential segment of the VV DNA cloned in a suitable bacterial plasmid;
2) The VV DNA sequences located on either side should permit homologous recombinations to take place in vivo in the plasmid and the viral genome. A reciprocal double recombination leads to a transfer of the plasmid DNA insert into the viral genome in which it is propagated and expressed (Panicali and Paoletti, 1982; Mackett et al., 1982; Smith et al., 1983; Panicali et al., 1983).

SUMMARY OF THE INVENTION

The present invention relates to a vaccinia virus characterised in that it contains all or part of a DNA sequence coding for an antigenic glycoprotein of rabies, hereinafter called DNA sequence (I).

"Vaccinia virus" is understood to denote all or part of a virus of the Pox virus genus, in particular the subgenus Vaccinia, which incorporates, in addition to vaccinia itself, other viruses such as "Cowpox".

"Antigenic glycoprotein of rabies" is understood to denote a glycoprotein which, in vitro but preferably in vivo, has immunogenic characteristics identical or closely related to those of true rabies glycoprotein, that to say the glycoprotein of the wild type virus.

Although it is preferred to use for the DNA sequence (I) the DNA sequence coding for the complete mature protein, it is possible to use only a portion of this DNA sequence, or such a sequence bearing point mutations but which lead to products having quasi-identical activities. This virus will preferably contain the combination of elements providing for the expression of the said glycoprotein, in particular a vaccinia gene promoter such as the 7.5K gene promoter referred to as P 7.5K, which will be placed up-stream of the DNA sequence (I).

This promoter/DNA sequence (I) combination will be inserted into a vaccinia virus gene, for example the TK gene, and this will provide a possible means of selection, as will be explained below.

The hybrid virus thus obtained can be used as such, live or inactivated by chemical or physical treatment, as a vaccinating agent, or can alternatively be used to infect a cell culture from which the antigenic glycoprotein may be extracted from the ground cell preparation by known techniques.

To reduce to a minimum the risks of accidents when vaccinating with a live virus, it is also possible to envisage using a temperature-sensitive mutant of vaccinia (F. Keller et al., 1978 and F. Keller and R. Drillien, 1980).

This type of ts mutation can exist on the vaccine vector itself or alternatively can be introduced by mutation in the recombinant viruses according to the invention. In particular, it is possible to introduce different temperature-sensitivities in the recombinant virus in order to maintain the phenotype even in cases of partial reversion.

Furthermore, it is possible to provide for the use of a mutant vaccinia virus having a host specificity, which does not grow, or grows to only a small extent, on human cells, and the pathogenicity of which is still weaker than that of vaccinia.

The present invention relates, in addition, to vaccines intended for treating or preventing rabies, characterised in that they contain a hybrid virus according to the invention, or a glycoprotein, obtained by carrying out the above process.

The invention also relates to the antisera obtained from animals immunised with the vaccines according to the invention.

With these vaccines, the methods of administration can be varied, and in particular the intra dermal or oral route can be used. These vaccines can be administered with known pharmaceutical carriers, and contain in addition adjuvants which enable their vaccinating power to be increased.

BRIEF DESCRIPTION OF THE DRAWINGS

FIGS. 1A–1B show the cDNA and amino acid sequences for a rabies glycoprotein.

FIG. 3 shows the mutation step to obtain plasmid pTG155-Pro.

DETAILED DESCRIPTION OF THE INVENTION

The examples below are designed to demonstrate other characteristics and advantages of the present invention.

Figure 2:
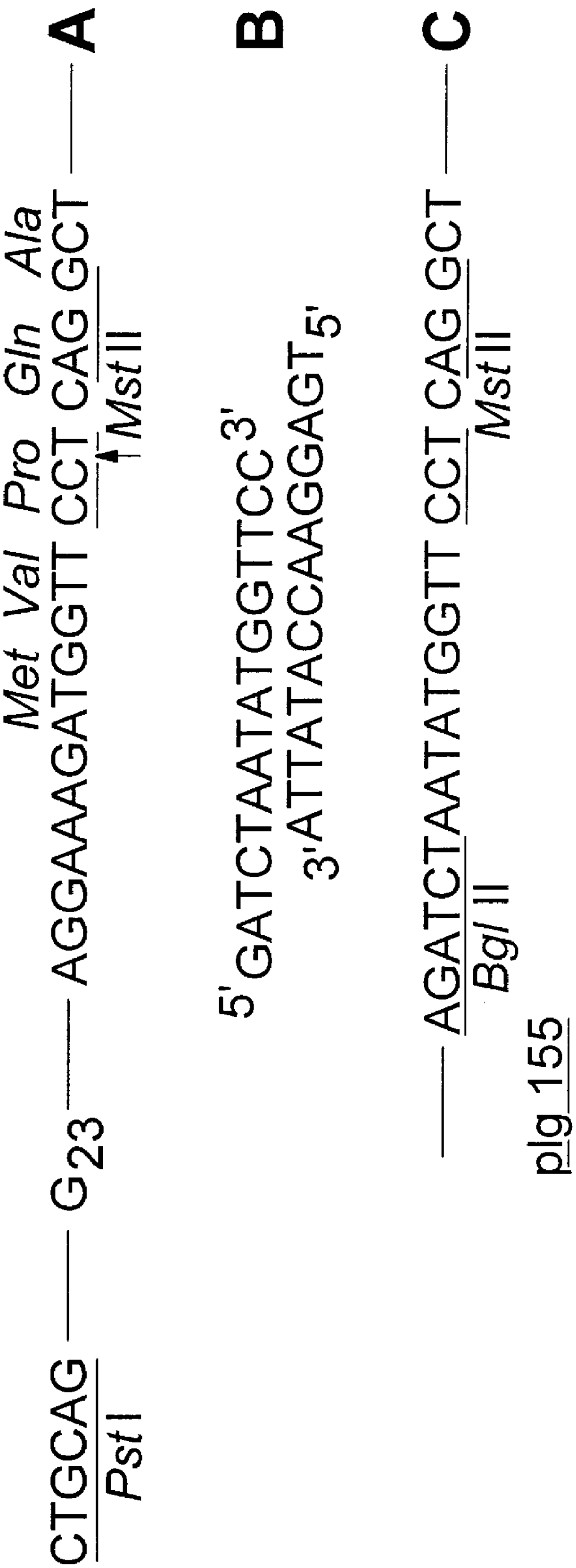
FIG. 2 shows the steps for obtaining plasmid pTG155.
Figure 5:
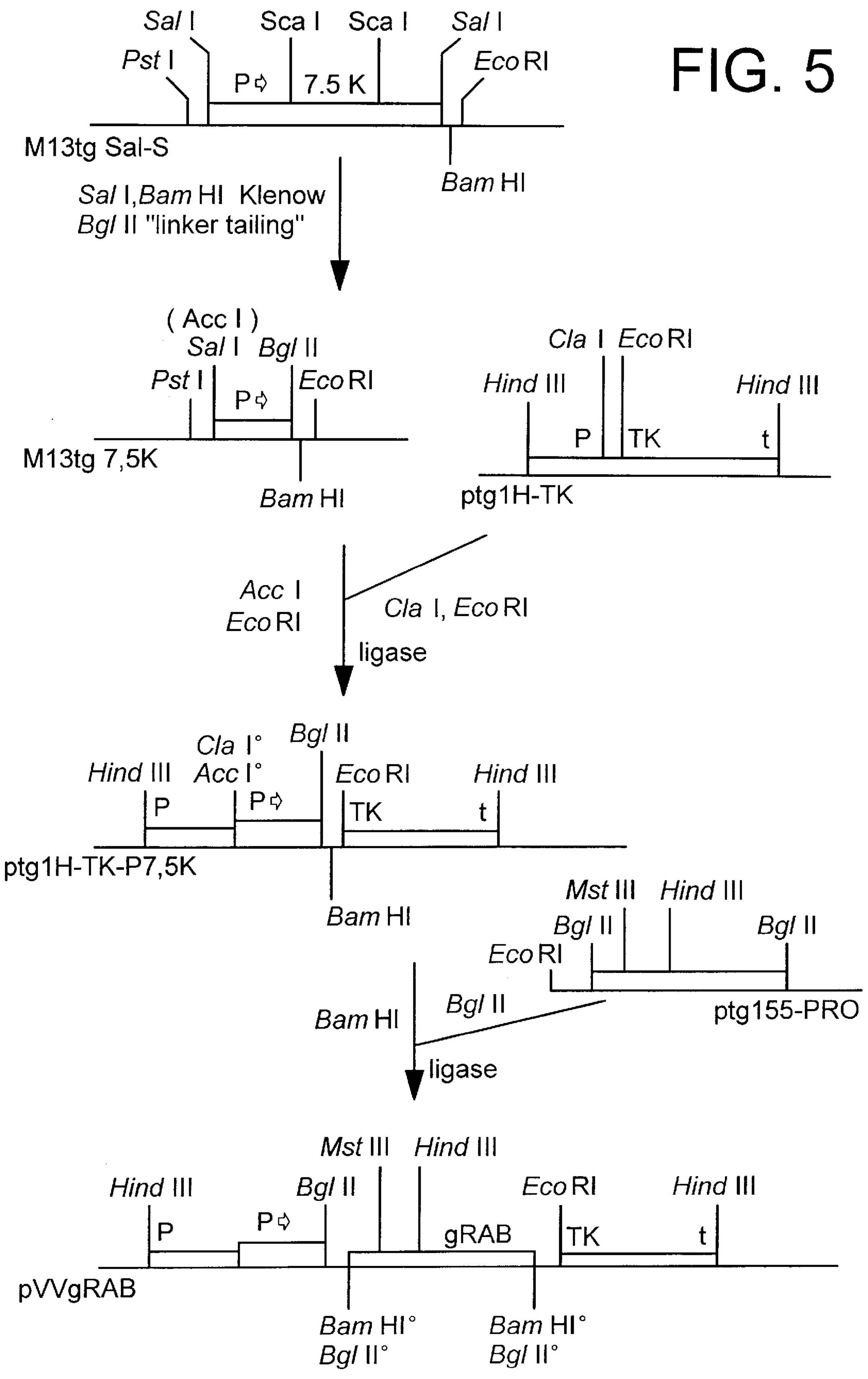
FIG. 5 shows the insertion of the 7.5K vaccinia promoter and the rabies glycoprotein cDNA into the TK gene.
Figure 6:
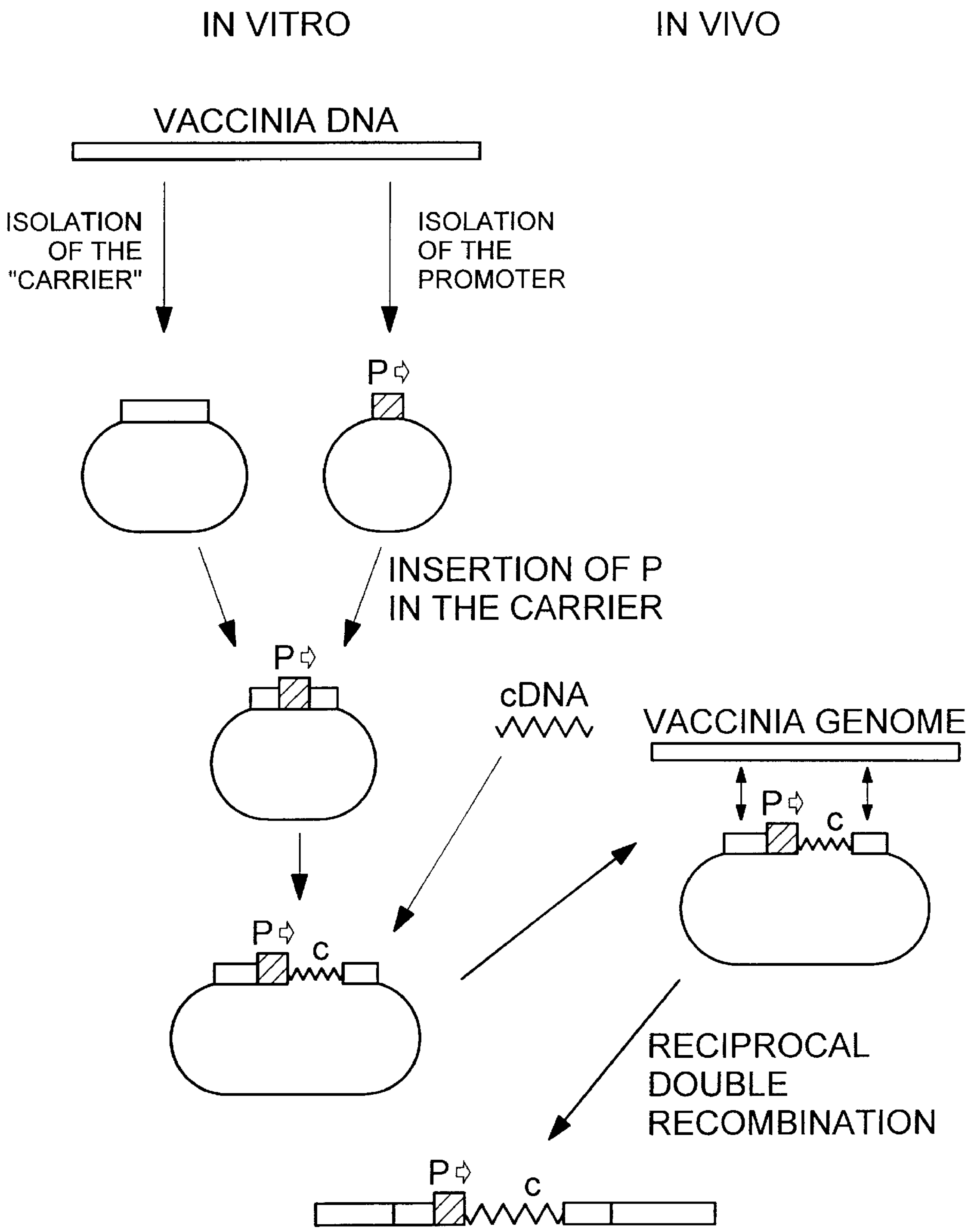
FIG. 6 shows the steps for cloning a plasmid of the invention in vaccinia virus.

The preparation of the virus according to the invention includes, in particular, the following stages:

1) Restructuring of one end of rabies cDNA, shown schematically in FIG. 1 [SEQ ID NO.:1], by the process shown schematically in FIG. 2 [SEQ ID NOS.:2–5], to obtain pTG155;
2) Mutation of one of the sequences of this cDNA in order to re-establish proline at the 8th amino acid in the glycoprotein, FIG. 3 [SEQ ID NOS.:6–10], to obtain pTG155-pro;
3) Synthesis of a mini-plasmid pTG1H from pBR322 (FIG. 4);
4) Insertion in this mini-plasmid of the Hin-J fragment bearing the TK gene of VV;
5) Insertion in the TK gene of the 7.5K protein promoter (FIG. 5);
6) Insertion under the P 7.5K promoter of the rabies gene carried by pTG155-pro (FIG. 5);
7) Cloning of the essential elements of this latter plasmid in vaccinia virus (FIG. 6).

The examples which follow illustrate the properties of the different components obtained.

The different materials used are identified in the examples.

Except where otherwise stated, the enzymes are used under the conditions recommended by the manufacturer and the techniques carried out are known to the specialist.

The amino acid sequences and nucleotide sequences shown in the figures are not listed in the body of the description to avoid encumbering it, but they constitute an integral part thereof.

Restructuring of the rabies glycoprotein cDNA

The sequence [SEQ ID NO.:1] coding for the rabies glycoprotein [SEQ ID NO.:12], published by Anilionis et al. and shown in FIG. 1, contains elements which can interfere with its translation and its expression as an antigen.

The rabies glycoprotein cDNA from plasmid pRG described by Anilionis et al. (1981), which is carried on a BglII-BglII fragment by different plasmids such as pTG147, pTG171 and pTG150, has already been described in French Patent No. 83/15716.

In the first place, the ATG corresponding to the initiation codon for the mature message is situated immediately adjacent to a polyG sequence introduced by the cDNA cloning procedure. This sequence is capable of causing instability during the recombination in vivo between the G/C elements at each of the ends of the cDNA and can in addition interfere with the translation of the message.

Then, the glycoprotein cDNA sequences do not correspond exactly with the sequence coding for the N-terminal portion of the mature glycoprotein. For this reason it was decided to remove these two obstacles before carrying out the cloning of the corresponding sequence.

Kozak (1981, 1983) has shown that the initiation codons of translation in eucaryotes are normally present in a sequence which can be represented in the following manner: A X X ATG (A or G), and alterations in this sequence can lead to reductions in translation. Although the importance of these end nucleotides is not fully established, it appears to be preferable to remove the adjacent G/C sequence and retain the essence of the consensus sequence mentioned above. Furthermore, it is necessary to provide for a BglII recognition sequence upstream, so as to facilitate subsequent manipulation.

By restructuring the 5' end of the cDNA, as shown in FIG. 2, advantage has been taken of a single MstII site which overlaps the codons coding for amino acids 2, 3 and 4 of the primary translation product.

In plasmid pTG150, the rabies glycoprotein cDNA of Anilionis has been inserted, by using PstI-BglII adaptor oligonucleotides (Lathe et al. 1982), in a single BglII site inserted in the HindIII site of plasmid pBR327 (Soberon et al., 1980).

This plasmid, represented by A [SEQ ID NO.:2] in FIG. 2, was partially digested with BglII and completely digested with MstII, and the appropriate linear fragments were isolated by gel electrophoresis on agarose having a low gellification temperature. The oligonucleotides (5'-dGATCTAATATGGTTCC-3') [SEQ ID NO.:3] and (5'-dTGAGGAACCATATTA-3') [SEQ ID NO.:4] were synthesised according to a technique described earlier (Kohli et al., 1982). The oligonucleotides [SEQ ID NOS.:3 and 4] are hybridised to give a partial duplex (B in FIG. 2) and inserted between the BglII and MstII ends of the purified linear plasmid, which enables recircularisation to take place and generates plasmid pTG155 (C [SEQ ID NO.:5] in FIG. 2).

The 8th amino acid of the mature glycoprotein (not possessing the signal sequence) of rabies virus strains ERA and CVS is proline, while in the cDNA isolated by Anilionis et al. there is found, in this position, a triplet coding for leucine.

In pTG155 shown in FIG. 3, the mutuant site is flanked by an upstream EcoRI site [SEQ ID NO.:6] in the vector and by a HindIII site [SEQ ID NO.:7] on the sequences corresponding to amino acids 10 and 11 of the sequence coding for the mature glycoprotein. This small EcoRI-HindIII fragment is cloned in bacteriophage M13tg131 (Kieny et al., 1983) in reverse orientation. Localised mutagenesis directed by an oligonucleotide is carried out according to the technique of Zoller and Smith (1983), using the oligonucleotide [SEQ ID NO.:9] (5'-dTACACGATCCCAGACAAGC-3') synthesised as mentioned above.

The codon for amino acid 8 in the cDNA sequence [SEQ ID NO.:10] is changed to replace CTA by CCA.

The oligonucleotide (19-mer) contains two modifications relative to the original sequence: a T in place of C, which corrects the triplet of leucine CTA to proline CCA, and an A in place of C which corresponds to a transversion in the GATA sequence. This generates a dam methylation sequence GATC which promotes the incorporation of the oligonucleotide sequence by correcting selective false pairings in vivo.

It should be noted that the EcoRI/HindIII fragment has been cloned in reverse orientation to that shown here so that the lower strand, complementary to the oligonucleotide, would be present in the single stranded M13 recombinant bacteriophage.

Areas of phage are examined for hybridisation under suitable conditions with the oligonucleotide labelled at its 5' end with $^{32}$p. A number of positive areas are withdrawn and the corresponding inserts are sequenced. The insert of one of the correctly modified clones is recloned in pTG155, exchanging the EcoRI/HindIII fragments to generate finally the restructured plasmid pTG155-pro. Analysis of the clones appearing during this stage is facilitated by the existence of a new site for the restriction enzyme Sau3A, which coincides with the dam methylation sequence introduced during the oligonucleotide-directed mutagenesis.

In plasmid pTG155-pro, the restructured rabies glycoprotein cDNA is flanked at each end by BglII sites. At the downstream end, the BglII site originates from the use of the BglII-PstI adaptor oligonucleotide octamer used for cloning the PstI-PstI cDNA fragment in the BglII site, and the upstream site results from the use of a small double-stranded oligonucleotide designed to remove the G/C end.

Construction of hybrid plasmids

The combined sizes of the different elements needed for transfer of the sequence coding for the rabies glycoprotein into the VV genome, and the subsequent expression thereof, are of the order of several kb. It has hence been deemed necessary to minimise the size of the replication plasmid in *E. coli* used for the construction work, so as to facilitate the necessary manipulations.

The HindIII (Hin-J) fragment of thee VV genome contains the complete thymidine kinase (TK) gene which has already been used previously to permit the exchange and recombination of DNA inserted in the VV genome (Mackett et al., 1982). It is important to note that the transfer of an insert in the TK gene into the VV genome creates a TK-deficient virus which can be recognised by simple selection.

In the first place, it was necessary to produce a small sized plasmid bearing a single HindIII site which could be used for integration of the VV Hin-J fragment. Moreover, it was necessary to remove the unnecessary restriction sequences of the plasmid so as to enable the following manipulations to be performed.

Figure 4:
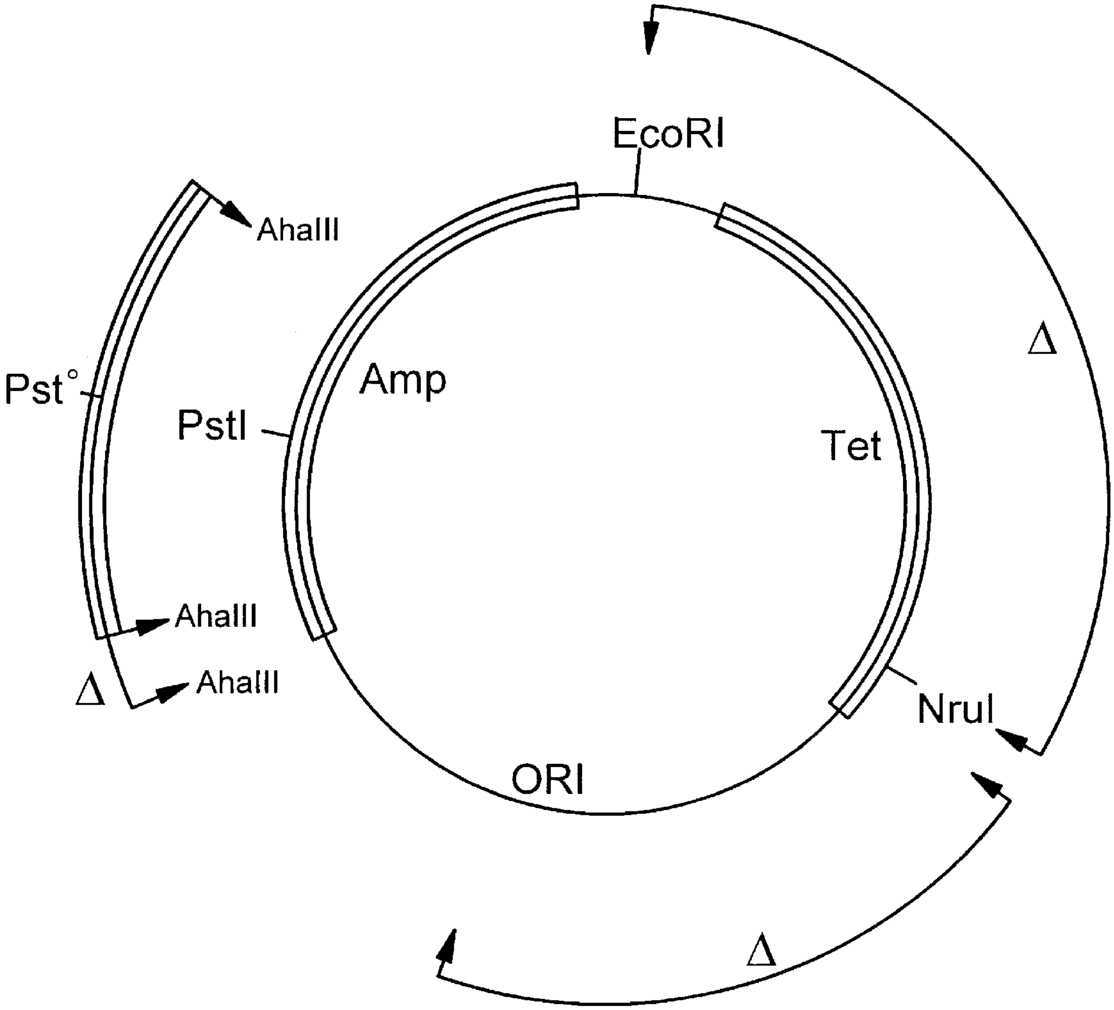
FIG. 4 shows the synthesis of mini-plasmid pTGIH.

The construction was primed starting from plasmid pML2 (Lusky and Botchan, 1981), which is a vector derived from plasmid pBR322 by spontaneous deletion in which the segment between nucleotide 1089 and 2491 has been lost (FIG. 4). The PstI sequence was first removed by inserting the AhaIII-AhaIII fragment of pUC8 (Vieira and messing, 1982) between two AhaIII sites of pML2, removing 19 base pairs. The "linker-tailing" method (Lathe et al., 1984) was used to insert a HindIII linker, treated with S1, between the NruI and EcoRI sites of this plasmid, removing the BamHI site. This leads to a plasmid of 2049 base pairs carrying the functional β-lactamase gene (which confers resistance to ampicillin) and containing in addition an origin of replication active in *E. coli* and a single HindIII restriction site.

This construction has been called pTG1H.

The Hin-J fragment of the VV DNA carrying the TK gene has previously been cloned in a vector originating from pBR327 (Drillien and Spehner, 1983). This 4.6 kb fragment was recloned in the HindIII site of pTG1H. A clone was selected in which the TK gene is situated distally relative to the gene coding for ampicillin resistance.

This pTG1H-TK construction was used as a carrier in the following experiment.

The following stage was to isolate a VV promoter which could be used to control the expression of the sequence coding for the inserted rabies glycoprotein. The promoter of an early gene coding for a 7,500-dalton (7.5K) protein has already been used successfully for an identical purpose (Smith et al., 1983), so this segment was isolated.

The 7.5K gene is located on one of the smallest SalI fragments (Sal-S fragment) of the VV type WR genome (Venkatasan et al., 1981). Since small fragments are cloned preferentially, a large proportion of the clones obtained by direct cloning of the VV type WR DNA cut with SalI in plasmid pBR322 carries the Sal-S fragment. This fragment is transferred to the vector bacteriophage M13mp701 (Kieny et al., 1983) by SalI digestion and religation, thereby leading to phage M13thSal-S.

In this clone, there is an ScaI site in immediate proximity to the initiation ATG of the 7.5K gene. Down-stream of the 7.5K gene, there are located single BamHI and EcoRI sites originating from the vector. The BamHI and ScaI sites are fused by way of a BglII linker [SEQ ID NO.:11] 5'-CAGATCTG-3' by the "linker" technique, after completing the ends generated by BamHI digestion with the Klenow fragment of polymerase. This process removes the ScaI site but reconstitutes the BamHI site and shifts the single EcoRI site downstream. At the same time, the SalI(AccI) site downstream is removed, and the upstream site hence becomes unique.

This construction is called M13tg7.5K.

Within the Hind-J fragment of the VV DNA there are located ClaI and EcoRI sites which are separated by approximately 30 base pairs (Weir and Moss, 1983). The 7.5K promoter fragment present in M13tg7.5K is excised with AccI and EcoRI and cloned between the ClaI and EcoRI sites of pTG1H-TK to generate pTG1H-TK-P7.5K, the synthesis of which is shown schematically in FIG. 5.

This construction leads to the transfer of the single BamHI site of the M13 vector immediately downstream of the 7.5K promoter sequence. This single BamHI site is used in the following constructions. pTG1H-TK-P7.5K is digested with BamHI and ligated with PTG155-pro digested with BglII (FIG. 5).

After transformation of *E. coli*, one of the recombinant plasmids isolated by this procedure, pVVgRAB, is selected, since it carries the cDNA of the rabies glyco-protein in the correct orientation for expression starting from the 7.5K promoter.

pVVgRAB will sometimes be referred to as pTG1H-TK-P7.5K-gRAB.

Cloning in vaccinia virus (FIG. 6)

The strategy described by Smith et al. (1983) rests on the exchange in vivo between a plasmid carrying an insert into the VV TK gene and the wild-type viral genome, so as to inactivate the TK gene carried by the virus. The $TK^-$ viruses can be selected by spreading on a TK-negative cell line in the presence of 5-bromodeoxyuridine (5BUdR) (Mackett et al., 1982). Thymidine kinase phosphorylates 5BUdR to 5'-monophosphate, which is then converted to triphosphate. This compound is a dTTP analog and its incorporation in DNA blocks the correct development of the virus. A $TK^-$ virus can nevertheless replicate its DNA normally and leads to visible plaques in a similarly $TK^-$ cell layer.

Vaccinia virus propagates in the cytoplasm of infected cells rather than in their nucleus. For this reason it is not possible to take advantage of the host machinery of DNA replication and transcription, and the virion has to possess the components for expression of the viral gene. Purified VV DNA is non-infectious.

In order to generate recombinants, it is necessary to carry out simultaneously cell infection with a VV and transfection with the cloned DNA segment which is of interest Nevertheless, generation of the recombinants is limited to a small proportion of the cells which are competent for transfection with DNA. For this reason, it was necessary to implement an indirect "congruence" strategy to reduce the background of non-recombinant parent virus. This was accomplished by using as live infectious virus a temperature-sensitive mutant (ts) of vaccinia which is not capable of propagation at a non-permissive temperature of 39.5° C. (Drillien and Spehner, 1983). When cells are infected with a ts mutant under non-permissive conditions and transfected with DNA of a wild-type virus, viral multiplication will occur only in the cells which are competent for transfection and in which recombination between the wild-type viral DNA and the genome of the ts virus has taken place; there will be no outcome in the other cells despite their having been infected. If a recombinant plasmid containing a vaccinia DNA fragment such as pVVgRAB is included in the transfection mixture at the appropriate concentration with the wild-type DNA, it is also possible to procure its participation in the homologous recombination with the vaccinia DNA in the competent cells.

Primary cell monolayers of chick embyro fibroblasts (CEF) are infected at 33° C. with VV-Copenhagen ts 26 (0.1 pfu/cell) and transfected with a calcium phosphate coprecipitate of VV-Copenhagen wild-type DNA (0.5 $\mu g/10^6$ cells) and recombinant plasmid pTG1H-TK-P7.5K-gRAB (3.0 $\mu g/10^6$ cells). It should be noted that, in the following experiments, the lower concentrations (0.1 $\mu g/10^6$ cells) gave substantially improved yields of recombinants.

After incubation for 2 hours at a temperature which does not permit development of the ts virus (39.5° C.), the cells are rinsed and incubated for 48 hours at 39.5° C. Dilutions of $ts^+$ virus are used to reinfect an L-$TK^-$ mouse cell monolayer at 37° C., and are incubated in the presence of 5BUdR (100 $\mu g$/ml). Various $TK^-$ plaques are obtained from these cells which have received the recombinant plasmid, while control cultures without plasmids do not show visible plaques.

Correct reciprocal double recombination between the hybrid rabies/vaccinia plasmid and the VV genome exchanges the TK viral gene for the TK gene carried by the insert present in the plasmid. In the VV genome, the TK gene is present on a single HindIII:Hin-J fragment. The recombinants which have transferred the expression block of the rabies glycoprotein are presumed to have integrated an internal HindIII site derived from the glycoprotein cDNA. For this reason the purified DNA from $TK^-$ virus is digested with HindIII and subjected to agarose gel electrophoresis. As was predictable, the 4.6 kb Hin-J fragment is absent, and on the other hand two new 1.1 and 5.5 kb fragments reveal the presence of an insert containing an internal HindIII site. After sub-cloning of the $TK^-$ viruses, one of the recombinants, VVgRAB-26D3, is preserved.

Expression of the rabies glycoprotein starting from recombinant vaccinia viruses Semi-confluent L-$TK^-$ cell monolayers are infected with VVgRAB-26D3 (50 pfu/cell) for 1 hour at room temperature, a methionine-free culture medium is then added, and after 30 min each culture dish is supplemented with [$^{35}$S]-l-methionine (1265 Ci/mmole) and incubation is continued at 37° C. for 4 hours. Cells are harvested, resuspended in an immunoprecipitation buffer containing protease inhibitors and, after ultrasonic rupture and clarification, the proteins bound by the anti-rabies antiserum are recovered by affinity chromatography on a protein A-sepharose resin, loaded on an electrophores is gel and fluorgraphed by a techique described by Lathe et al., (1980).

Figure 7:
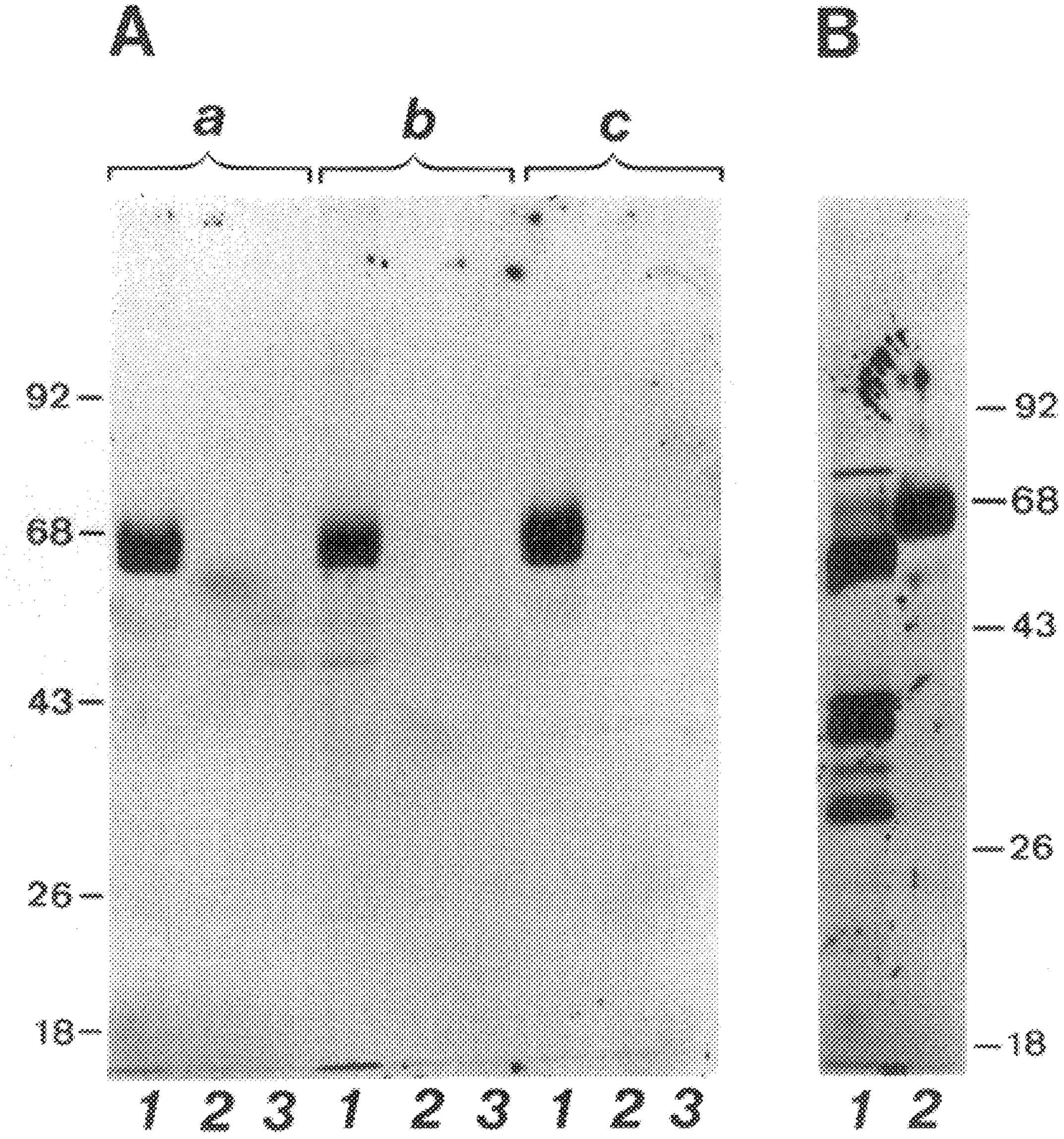
FIGS. 7A–B show the expression of the rabies glycoprotein from recombinant vaccinia viruses.

A polyclonal antiserum 3554-R215 prepared against the purified glycoprotein at the Wistar Institute was used in the experiments illustrated in FIG. 7, A (a) and B; identical results are obtained (b,c) with two monoclonal antibodies neutralising the viruses (Wistar 509-6 and 101-1) which identify different epitopes on the rabies glycoprotein. In A the cell monolayer is infected with:

1) the VVgRAB-26D3 recombinant, 2) the wild-type vaccinia virus, 3) no virus.

In B a cell monolayer is infected with VVgRAB-26D3 and labelled in the presence (1) or absence (2) of tunicamycine (2 $\mu g$/ml).

In A and B the standard molecular weights are given in kilodaltons.

As is seen in FIG. 7A, a polyclonal rabies antiserum, and likewise two monoclonal antibodies neutralising the virus, precipitate a protein which migrates in the form of a diffuse band with an apparent molecular weight of approximatey 66,000 daltons. This molecular weight corresponds exactly to the weight, 67,000 daltons, of an authentic rabies glycoprotein.

Since the molecular weight of the natural glycoprotein and the recombinant correspond, it was verified that the recombinant glycoprotein was glycosylated in vivo. A cell monolayer was infected with VVgRAB-26D3 as above, and to the medium there was added, before the labelling, a powerful inhibitor of glycosylation, tunicamycin (2 $\mu g$/ml). The infected cell extracts are immunoprecipitated using a polyclonal antibody and the product is loaded on an electrophoresis gel as above. As shown in FIG. 7B, the addition of tunicamycin to the medium leads to a reduction in the molecular weight of the 66,000-dalton recombinant glycoprotein, which corresponds to the removal of the glycosylated groups of the protein. It may hence be concluded from this that the recombinant rabies glycoprotein is glycosylated in the cells infected with VVgRAB. Various additional bands in lane (1) are presumed to be degradation products of the non-glycosylated rabies antigen.

In another experiment, an L-$TK^-$ cell monolayer is infected with VVgRAB-26D3 ($10^5$ pfu per plaque containing $10^6$ cells) and incubated for 8 hours at 37° C. The cells are fixed, and treated with monoclonal and polyclonal antibodies and, after very thorough washing, the bound antibody is detected using a second antibody (goat anti-mouse) labelled with fluorescein. The majority of the cells infected with the VVgRAB-26D3 recombinant (A) show significant fluorescence, whereas uninfected cells (C) and cells infected with non-recombinant viruses (B) do not show fluorescence.

Figure 8:
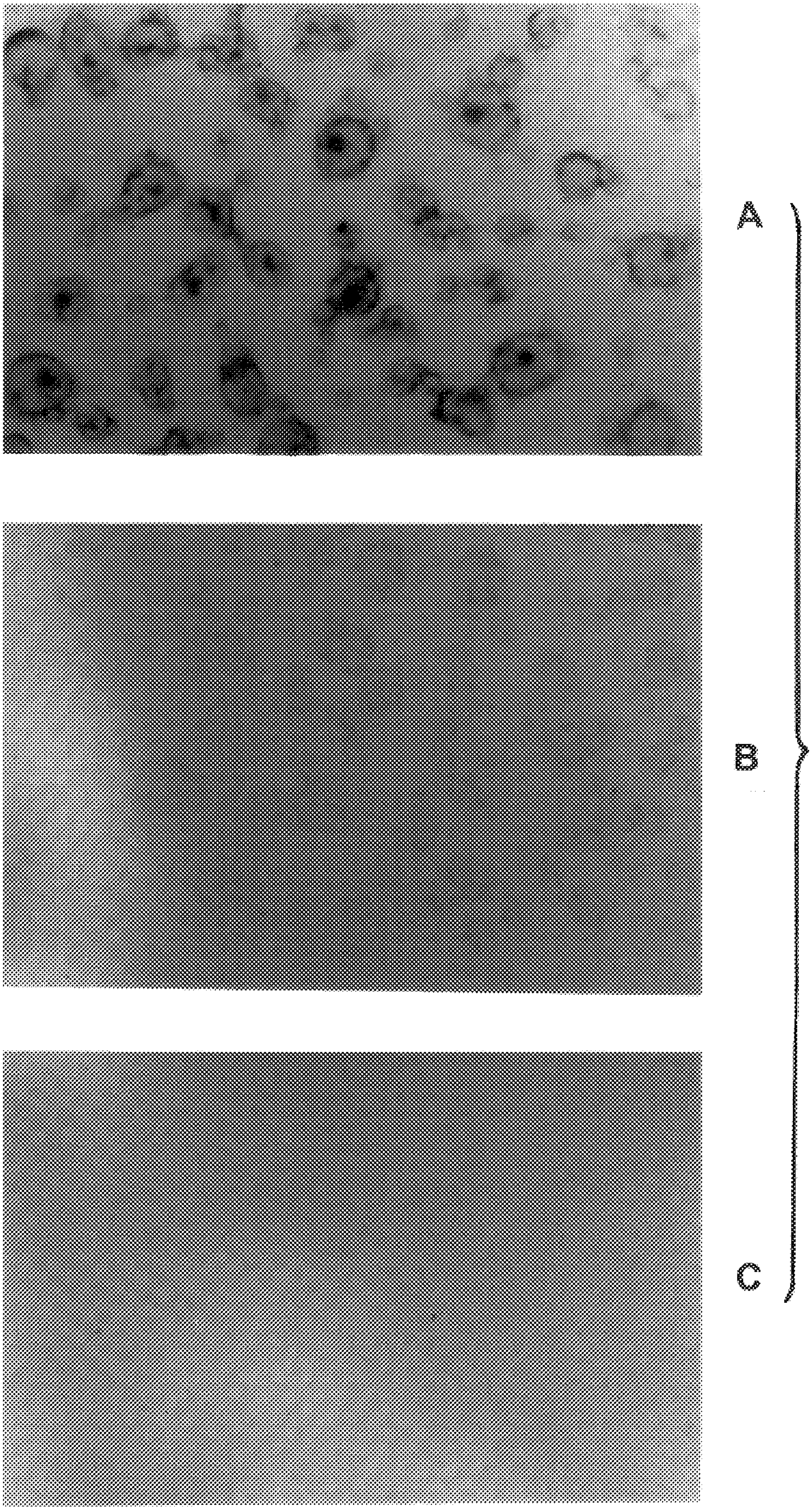
FIGS. 8A–C show fluorescence patterns of cells infected by recombinant vaccinia viruses, uninfected cells and cells infected with non-recombinant vaccinia viruses.

As is brought out by FIG. 8, the fluorescence is associated predominantly with the cytoplasmic membrane, as could be expected of a transmembrane protein.

Immunological properties in vivo of the live hybrid vaccinia/rabies virus

Rabbits are immunised intradermally with $3\times10^7$ pfu of VVgRAB-26D3, and samples of serum are withdrawn after 0, 11 and 14 days. A recognisable swelling is observed at the site of infection which decreases after 8 to 9 days. An ERA rabies virus strain inactivated with β-propiolactone is labelled with $^{125}I$ according to the standard protocol and tested for its reaction with the serum of the immunised animals.

The bound proteins are placed on electrophoresis gel and autoradiographed.

The 11- and 14-day sera, but not the serum of control day 0, were found to recognise and effectively bind the radio-labelled viral glycoprotein. The serum of control animals immunised with Copenhagen type non-recombinant vaccinia virus does not show such reactions. The serum of the immunised animals described above is then tested for inactivation of rabies viruses in vitro. The dilutions of rabies strain ERA are preincubated for 1 hour with different amounts of the rabbit antiserum, and plated on new born hamster kidney (BHK) cells on microtitration plates ($10^3$ cells/well). After incubation at 37° C. for 22 hours, the productive infected cells are stained using a direct immunofluorescence technique.

Table I shows that, even at the greatest dilutions of the 11- and 14-day antiserum, complete inactivation of the virus is obtained. The preimmune and non-recombinant sera do not give detectable neutralisation. The titres are given as the greatest dilution at which inhibition of infection is observed.

TABLE 1

| No. of days after vaccination | VVgRAB26D3 Rabbit I | Rabbit II | Rabbit III | Rabbit IV | Wild-type vaccinia |
|---|---|---|---|---|---|
| 0 | 0 | 0 | 0 | 0 | 0 |
| 11 | 10,000 | 10,000 | 10,000 | 10,000 | 0 |
| 14 | >30,000 | >30,000 | >30,000 | >30,000 | 0 |

These results show that, not only does the VVgRAB-26D3 recombinant induce production of antibodies which react with rabies virus, but also that the antiserum of immunised animals is capable of inactivating rabies virus in vitro. The induction of neutralising antibodies does not always corollate with protection against the development of the disease. For this reason, a direct study has been carried out of a test of protection using the recombinant virus. Mice are immunised by injection in the leg or by scratching the tail with $10^7$ pfu of live VVgRAB-26D3. These animals are then inoculated with a lethal dose (1,000 $LD_{50}$ units) of a wild-type rabies virus introduced by intracerebral injection. After 10 days, the group of control animals immunised with non-recombinant vaccinia show terminal rabid infection, which in contrast 15 out 15 animals immunised with VVgRAB-26D3 show no trace of disease.

It may therefore be concluded that immunisation with the live vaccinia/rabies recombinant virus leads to protection against rabies.

Immunological properties in vivo of the inactivated hybrid vaccinia/rabies virus Three types of inactivated vaccine can be prepared from cells infected with vaccinia/rabies recombinant virus: either a crude extract of infected cells, or purified intact virus, or purified glycoprotein G. The three preparations are inactivated with β-propiolactone.

BHK cells infected with VVgRAB-26D3 are homogenised in a Dounce grinder and the centrifugation supernatant represents the crude cell extract.

To obtain the killed purified virus, this preparation is inactivated with 1/4,000 β-propiolactone and centrifuged on a sucrose gradient according to conventional techniques.

The purified glycoprotein G is obtained by solubilisation of the crude extract in the presence of 2% strength Triton X-100. After centrifugation for 1 hour at 100,000 g, G is isolated from the supernatant by passage on an affinity column prepared with a monoclonal anti-G antibody. This purified glycoprotein G is also inactivated with β-propiolactone Mice are immunised with two intraperitoneal injections of 0.5 ml of these inactivated preparations at an interval of 1 week, and subjected to the test 1 week later (240 $LD_{50}$ units) by the intracerebral route.

Table II shows the anti-rabies antibodies measured 5 on days 7 and 14.

TABLE II

| | Amount of injected protein in μg/mouse | Titre of anti-rabies antibodies Day 7 | Day 14 |
|---|---|---|---|
| VVgRAB-26D3 crude extract | 140 | 80 | 8,000 |
| VVgRAB-26D3 purified virus | 9 | 270 | 4,000 |
| VVgRAB-26D3 purified G | 50 | 120 | 15,000 |
| Copenhagen type vaccinia crude extract | 900 | 10 | 10 |

All the animals vaccinated with the different preparations of inactivated vaccine derived from VVgRAB-26D3 survive the intracerebral injection of rabies virus, whereas the animals of the control group die at the expected time.

It is important to note that, even when inactivated, the hybrid VVgRAB6D3 virus confers effective protection against experimental rabies infection. This shows that, in the intact recombinant virus, the rabies glycoprotein is presented at the surface of the virion and is capable of inducing an immunological response similar to that induced by inactivated rabies virus.

Vaccination of foxes and vaccination by the oral route

In Western Europe, the fox is the main agent of dissemination of rabies. It is therefore of basic importance to be able to control the vaccination of foxes. This will preferably be carried out by the oral route in order to minimise handling of the animals.

Red foxes (Vulpes vulpes) less than one year old are immunised by various routes with $10^8$ pfu of live VVgRAB-26D3. The controls consist of two foxes vaccinated with classical killed anti-rabies vaccine and 4 foxes vaccinated with wild-type vaccinia.

Table III gives the anti-rabies antibody titre measured on days 7, 14 and 28. This table shows that, in foxes as in mice, the vaccinia/rabies recombinant virus induces production of antibodies comparable to that induced by the classical vaccine.

Vaccinated animals are subjected to the test of injection of virulent rabies virus on day 28.

The foxes vaccinated with wild-type virus die a+ the expected time. All the foxes vaccinated with the classical killed vaccine or with VVgRAB-26D3 [even the fox (2) inoculated subcutaneously which had no serum-neutralising antibodies] are alive 2 months after the test.

| Vaccine used | Inoculation route | | Antibody titre* Day 6 | Day 14 | Day 18 |
|---|---|---|---|---|---|
| Killed classical | Subcutaneous | (1) | 0.33 | 0.64 | 0.24 |
| | | (2) | 0.07 | 0.05 | 0.07 |
| Wild-type vaccinia | Intradermal | | — | — | — |
| VVgRAB-26D3 | Intradermal | (1) | 0.64 | 6.1 | 4.4 |
| | | (2) | 0.05 | 0.6 | 1.67 |
| VVgRAB-26D3 | Subcutaneous | (1) | 0.46 | 2.32 | 4.3 |
| | | (2) | — | — | — |
| VVgRAB-26D3 | Oral with scarification of the mucosa | (1) | 0.33 | 0.88 | 1.67 |
| | | (2) | 0.24 | 0.88 | 2.31 |

*The antibody titres are expressed in international units (reference serum - 65 I.U. - neutralising at $10^{-4.2}$)

The following strain has been filed in the Collection Nationale de Cultures de Microorganismes (CNCM) (National Collection of Microorganism Cultures) –28, rue de Docteur Roux, 75724 PARIS CEDEX 15: *E. coli* TGE1106 transformed by pTG171 No. I-248 filed on 30th Sep. 1983.

REFERENCES

Anilionis, A., Wunner, W. H. & Curtis, P. J. (1931) Nature 294, 275–278.

Drillien, R. & Spehner, D. (1983) Virology 131, 385–393.

Kieny, M. P., Lathe, R. & Lecocq, J. P. (1983) Gene 26, 91–99.

Kohli, V., Balland, A., Wintzerith, M., Sauerwald, R.,

Staub, A. & Lecocq, J. P. (1982) Nucleic Acids Res. 10, 7439–7448.

Kozak, M. (1981) Nucleic Acid Res. 9, 5233–5252.

Kozak, M. (1983) Microbiol. Rev. 47, 1–45.

Lathe, R., Hirth, P., Dewilde, M., Harford, N. & Lecocq, J. P. (1980) Nature 284, 473–474.

Lathe, R., Balland, A., Kohli, V. & Lecocq, J. P. (1982) Gene 20, 187–195.

Lathe, R., Kieny, M. P., Schmitt D., Curtis, P. & Lecocq, J. P. (1984a) J. Mol. Appl. Genet., in press.

Lathe, R., Kieny, M. P., Skory, S. & Lecocq, J. P. (1984a) DNA, in press.

Lusky, M., Botchan, M. (1981) Nature 293, 79–81.

Mackett, M., Smith, J. L. & Moss, B., (1982) Proc. Natl. Acad. Sci. U.S.A. 79, 7415–7419.

Panicali, D. & Paoletti, E. (1982), Proc. Natl. Acad. Sci. U.S.A. 79, 4927–4931. Panicali, D., Davis, S. W., Weinberg, R. L. & Paoletti, E. (1983) Proc. Natl. Acad. Sci. U.S.A. 80, 5364–5368.

Smith, G. L., Mackett, M. & Moss, V. (1983) Nature 302, 490–495.

Soberon et al., Gene 9, 287–305 (1980).

Venkatesan, S., Baroudy, S. M. & Moss, B. (1981) Cell 125, 805–813.

Vieira, J. & Messing, J. (1982) Gene 19, 259–268.

Weir, J. P. & Moss, B. (1983) J. Virol. 46, 530–537.

Wiktor, T. J. (1978) Develop. Biol. Standard 40, 255–264.

Wiktor, T. J. (1980) in *Rhabdoviruses* III pp. 99–112 (ed. D. H. L. Bishop) CRC Press, Inc.

Wunner, W. H., Dietzschold, B., Curtis, P. J. & Wiktor, T. J. (1983) J. Gen. Virol. 64, 1649–1659.

Yelverton, E., Norton, S., Obijeski, J. F. & Doeddel, D. V. (1983) Science 219, 614–620.

Zoller, M. J. & Smith, M. (1983) in *Methods in Enzymology,* Vol. 100, pp. 468–500 (Eds. Wu, R., Grossman, L., Moldave, K.) Academic Press, London.

Keller F., Drillien R. and Kirn A.: Thermosensibilité du developpement des poxvirus et virulence. Utilisation de souches thermosensibles comme vaccin. Rencontre Biologique, 1978 (L. Hartmann), p. 121–126, Ed. Varia, Paris.

Keller F. and Drillien R.: Un mutant thermosensible atténué du virus vaccinal. Ann. Virol. (INSTITUT PASTEUR), 1980, 131 E, 85–94.

We claim:

1. An oral vaccine for preventing or treating rabies in a mammal comprising a hybrid vaccinia virus that contains and expresses a DNA sequence encoding the amino acid sequence rabies glycoprotein G wherein said DNA sequence is present in a non-essential segment of vaccinia virus and a pharmaceutically acceptable carrier.

2. The vaccine according to claim 1 wherein said hybrid vaccinia virus is live.

3. The vaccine according to claim 1, wherein said rabies glycoprotein G has the first 8 N-terminal amino acids of SEQ ID NO: 1 wherein the amino acid at position 8 has been mutated from Leu to Pro.

4. The vaccine according to claim 3, wherein said hybrid vaccinia virus is live.

5. The vaccine according to claim 3, wherein said rabies glycoprotein G has the amino acid sequence as depicted in FIG. 1*a–b* (SEQ ID NO.: 1) starting from Lysine in position 1 and replacing the Leucine residue in position 8 with a Proline residue.

6. The vaccine according to claim 3, wherein said rabies glycoprotein G is under the control of the 7.5K vaccinia promoter and is present in the vaccinia thymidine kinase gene.

7. The vaccine according to claim 1, wherein said hybrid vaccinia virus is temperature sensitive.

8. The vaccine according to claim 1, wherein said DNA sequence is present in a vaccinia thymidine kinase gene.

9. The vaccine according to claim 1, wherein said rabies glycoprotein G DNA sequence is under the control of a vaccinia promoter.

10. The vaccine according to claim 9, wherein said rabies glycoprotein G DNA sequence is under the control of a 7.5K vaccinia virus promoter.

11. The vaccine according to claim 1, wherein said rabies glycoprotein G DNA sequence codes for the complete mature protein.

12. The vaccine according to claim 1, wherein said rabies glycoprotein G is preceded by a signal sequence as depicted in FIG. 1*a–b* (SEQ ID No.: 1) from position −19 to −1.

13. The vaccine according to claim 1, wherein said hybrid vaccinia virus is temperature sensitive.

14. A method of preventing or treating rabies in a mammal comprising orally administering to said mammal a hybrid vaccinia virus that contains and expresses a DNA sequence encoding rabies glycoprotein G wherein said DNA sequence is present in a non-essential segment of vaccinia virus, in an amount sufficient to prevent or treat rabies.

15. The method of preventing rabies according to claim 14, wherein said rabies glycoprotein G has the first 8 N-terminal acids of SEQ ID NO: 1 wherein the amino acid at position 8 has been mutated from Leu to Pro.

16. The method of preventing or treating rabies according to claim 15, wherein said rabies glycoprotein G has the amino acid sequence as depicted in FIG. 1 *a–b* (SEQ ID NO.: 1) starting from Lysine in position 1 and replacing the Leucine residue in position 8 with a Proline residue.

17. The method of preventing or treating rabies according to claim 15, wherein said rabies glycoprotein G is under the control of the 7.5K vaccinia promoter and is present in the vaccinia thymidine kinase gene.

18. The method of preventing or treating rabies according to claim 14, wherein said DNA sequence is present in a vaccinia thymidine kinase.

19. The method of preventing or treating rabies according to claim 14, wherein said rabies glycoprotein G sequence is under the control of a vaccinia promoter.

20. The method of preventing or treating rabies according to claim 19, wherein said rabies glycoprotein G DNA sequence is under the control of a 7.5K vaccinia virus promoter.

21. The method of preventing or treating rabies according to claim 14, wherein said rabies glycoprotein G DNA sequence codes for the complete mature protein.

22. The method of preventing or treating rabies according to claim 14, wherein said rabies glycoprotein G is preceded by a signal sequence as depicted in FIG. 1*a–b* (SEQ ID NO.: 1) from position −19 to −1.

23. The method preventing or treating rabies according to claim 14, wherein said hybrid vaccinia virus is temperature sensitive.

24. The method of preventing or treating rabies according to claim 14, wherein said hybrid vaccinia virus is live.

25. The method of preventing or treating rabies according to claim 14, wherein said hybrid vaccinia virus is inactivated.

26. A method for preventing or treating rabies in a mammal comprising the steps of:

a) preparing a hybrid vaccinia virus containing and expressing a DNA sequence encoding the amino acid sequence of rabies glycoprotein G, wherein said DNA sequence is inserted within a non-essential region of said vaccinia virus; and b) orally administering said hybrid vaccinia virus to said mammal in an amount sufficient to prevent rabies.

27. The method for preventing or treating rabies according to claim 26, wherein said hybrid vaccinia virus is administered to said mammal as a pharmaceutical product having a preventive activity against rabies.

28. The method for preventing or treating rabies according to claim 26, wherein said pharmaceutical product contains a pharmaceutically acceptable vehicle.

29. The method for preventing or treating rabies according to claim 26, wherein said mammal is a fox.

30. The method for preventing or treating rabies according to claim 26, wherein said virus is temperature sensitive.

31. The method for preventing or treating rabies according to claim 26, wherein said rabies glycoprotein G has the first 8 N-terminal amino acids of SEQ ID NO: 1 wherein the amino acid at position 8 has been mutated from Leu to Pro.

32. The method for preventing rabies according to claim 26, wherein said hybrid vaccinia virus is live.

33. The method for preventing or treating rabies according to claim 26, wherein said DNA sequence is present in a vaccinia thymidine kinase gene.

34. The method for preventing or treating rabies according to claim 26, wherein said rabies glycoprotein G DNA sequence is under the control of a 7.5K vaccinia virus promoter.

35. The method for preventing or treating rabies according to claim 26, wherein said amino acid sequence of rabies glycoprotein G is depicted in FIG. 1*a–b* (SEQ ID NO.: 1) starting from Lysine residue in position 1 and replacing the Leucine residue in position 8 with a Proline residue, and wherein said 7.5K vaccinia virus promotor is placed upstream of the DNA sequence.

36. The method for preventing or treating rabies according to claim 35, wherein said amino acid sequence is preceded by a signal sequence as depicted in FIG. 1*a–b* (SEQ ID NO.: 1) from position −19 to −1.

* * * * *

UNITED STATES PATENT AND TRADEMARK OFFICE

CERTIFICATE OF CORRECTION

PATENT NO. : 5,830,477

DATED : November 3, 1998

INVENTOR(S) : Richard W. Lathe et al.

It is certified that error appears in the above-identified patent and that said Letters Patent is hereby corrected as shown below:

Title page, Related U.S. Application Data and after "Dec. 24, 1985, abandoned", please insert --,filed as PCT/FR85/00096, April 24, 1985 published as WO85/04810, Nov. 7, 1985.--

Signed and Sealed this

Sixth Day of June, 2000

Attest:

Q. TODD DICKINSON

*Attesting Officer* *Director of Patents and Trademarks*

UNITED STATES PATENT AND TRADEMARK OFFICE

CERTIFICATE OF CORRECTION

PATENT NO. : 5,830,477
DATED : November 3, 1998
INVENTOR(S) : Richard W. Lathe et al.

It is certified that error appears in the above-identified patent and that said Letters Patent is hereby corrected as shown below:

Title page,
Item [63], Related U.S. Application Data, delete "Dec. 24, 1985, --.

Signed and Sealed this

Fourteenth Day of January, 2003

JAMES E. ROGAN
*Director of the United States Patent and Trademark Office*